(12) United States Patent
Stubbs et al.

(10) Patent No.: US 8,364,261 B2
(45) Date of Patent: Jan. 29, 2013

(54) CARDIAC PACEMAKER WITH PACING RATE MONITORING

(75) Inventors: Scott Stubbs, Maple Grove, MN (US); Conrad L. Sowder, Minneapolis, MN (US); William J. Linder, Golden Valley, MN (US); Lynn S. Elliott, Maple Grove, MN (US); Kenneth P. Hoyme, Plymouth, MN (US); Hiten J. Doshi, Plymouth, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 264 days.

(21) Appl. No.: 12/916,881

(22) Filed: Nov. 1, 2010

(65) Prior Publication Data

US 2011/0046689 A1 Feb. 24, 2011

Related U.S. Application Data

(62) Division of application No. 11/316,682, filed on Dec. 22, 2005, now Pat. No. 7,826,897.

(51) Int. Cl.
*A61N 1/362* (2006.01)

(52) U.S. Cl. .......................................... 607/9

(58) Field of Classification Search ...... 607/9; 600/508, 600/509
See application file for complete search history.

(56) References Cited

U.S. PATENT DOCUMENTS

| | | | |
|---|---|---|---|
| 4,969,460 A | 11/1990 | Callaghan et al. |
| 5,016,630 A | 5/1991 | Moberg |
| 5,190,035 A | 3/1993 | Salo et al. |
| 5,209,228 A | 5/1993 | Cano et al. |
| 5,237,992 A | 8/1993 | Poore |
| 5,282,838 A | 2/1994 | Hauser et al. |
| 5,284,491 A | 2/1994 | Sutton et al. |
| 5,309,919 A | 5/1994 | Snell et al. |
| 5,372,607 A | 12/1994 | Stone et al. |
| 5,374,281 A | 12/1994 | Kristall et al. |
| 5,487,755 A | 1/1996 | Snell et al. |
| 5,507,786 A | 4/1996 | Morgan et al. |
| 5,549,654 A | 8/1996 | Powell |
| 5,690,689 A | 11/1997 | Sholder |
| 5,702,424 A | 12/1997 | Legay et al. |
| 5,720,771 A | 2/1998 | Snell |
| 5,782,886 A | 7/1998 | Kuiper et al. |
| 5,861,011 A | 1/1999 | Stoop |
| 5,891,175 A | 4/1999 | Walmsley et al. |
| 5,948,005 A | 9/1999 | Valikai et al. |
| 5,968,081 A | 10/1999 | Levine |
| 5,974,341 A | 10/1999 | Er et al. |
| 5,991,659 A | 11/1999 | de Vries et al. |
| 6,070,101 A | 5/2000 | Struble et al. |
| 6,141,586 A | 10/2000 | Mower |
| 6,161,042 A | 12/2000 | Hartley et al. |
| 6,240,313 B1 | 5/2001 | Esler |
| 6,246,909 B1 | 6/2001 | Ekwall |
| 6,430,439 B1 | 8/2002 | Wentkowski et al. |
| 6,459,928 B2 | 10/2002 | Mika et al. |

(Continued)

OTHER PUBLICATIONS

"U.S. Appl. No. 10/744,952, Advisory Action mailed Jul. 24, 2006", 3 pgs.

(Continued)

*Primary Examiner* — Brian T Gedeon
(74) *Attorney, Agent, or Firm* — Schwegman Lundberg & Woessner, P.A.

(57) ABSTRACT

A pacing monitoring system is described for incorporation in an implantable pacemaker that monitors the pacing rate and/or cumulative pace count in order to protect a patient from excessive pacing. The system includes monitoring circuitry that is configured to operate in multiple monitoring zones, where each zone is adapted to prevent excessively high-rate pacing during a particular mode of device operation.

20 Claims, 2 Drawing Sheets

U.S. PATENT DOCUMENTS

| | | |
|---|---|---|
| 6,477,420 B1 | 11/2002 | Struble et al. |
| 6,480,742 B2 | 11/2002 | Stahmann et al. |
| 6,665,558 B2 | 12/2003 | Kalgren et al. |
| 6,708,061 B2 | 3/2004 | Salo et al. |
| 6,748,261 B1 | 6/2004 | Kroll et al. |
| 6,904,317 B2 | 6/2005 | Florio et al. |
| 6,941,167 B2 | 9/2005 | Stahmann et al. |
| 7,194,307 B2 | 3/2007 | Salo et al. |
| 2002/0082663 A1 | 6/2002 | Stahmann et al. |
| 2004/0082973 A1 | 4/2004 | Kim et al. |
| 2005/0137633 A1 | 6/2005 | Salo et al. |
| 2007/0150010 A1 | 6/2007 | Stubbs et al. |

OTHER PUBLICATIONS

"U.S. Appl. No. 10/744,952, Final Office Action mailed Apr. 18, 2006", 9 pgs.

"U.S. Appl. No. 10/744,952, Non Final Office Action mailed Jul. 8, 2005", 9 pgs.

"U.S. Appl. No. 10/744,952, Non Final Office Action mailed Nov. 23, 2005", 8 pgs.

"U.S. Appl. No. 10/744,952, Notice of Allowance mailed Nov. 9, 2006", 4 pgs.

"U.S. Appl. No. 10/744,952, Response filed Mar. 23, 2006 to Non Final Office Action mailed Nov. 23, 2005", 7 pgs.

"U.S. Appl. No. 10/744,952, Response filed Jul. 18, 2006 to Final Office Action mailed Apr. 18, 2006", 9 pgs.

"U.S. Appl. No. 10/744,952, Response filed Nov. 8, 2005 to Non Final Office Action mailed Jul. 8, 2005", 11 pgs.

"U.S. Appl. No. 11/316,682 Notice of Allowance mailed Jun. 30, 2010", 6 pgs.

"U.S. Appl. No. 11/316,682, Non-Final Office Action mailed Oct. 15, 2009", 6 pgs.

"U.S. Appl. No. 11/316,682, Response filed Jan. 15, 2010 to Non Final Office Action mailed Oct. 15, 2009", 8 pgs.

"U.S. Appl. No. 11/316,682, Response filed Jul. 24, 2009 to Restriction Requirement mailed Jun. 24, 2009", 8 pgs.

"U.S. Appl. No. 11/316,682, Restriction Requirement mailed Jun. 24, 2009", 6 pgs.

"U.S. Appl. No. 11/316,682, Notice of Allowance mailed Mar. 18, 2010", 5 pgs.

CARDIAC PACEMAKER WITH PACING RATE MONITORING

CLAIM OF PRIORITY

This application is a divisional of and claims the benefit of priority under 35 U.S.C. §120 to U.S. patent application Ser. No. 11/316,682, now U.S. Pat. No. 7,826,897, filed on Dec. 22, 2005, which is hereby incorporated by reference herein in its entirety.

FIELD OF THE INVENTION

This invention pertains to methods and devices for delivering therapy to the heart with electrical stimulation.

BACKGROUND

Cardiac rhythm management devices are implantable battery-powered devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers have been used is in the treatment of bradycardia, where the ventricular rate is too slow. If functioning properly, the pacemaker makes up for the heart's inability to pace itself at an appropriate rhythm in order to meet metabolic demand by enforcing a minimum heart rate and/or artificially restoring AV conduction. Implantable devices may also be configured to treat tachyarrhythmias such as tachycardia and fibrillation with electrical stimulation. An implantable cardioverter/defibrillator (ICD) provides this kind of therapy by delivering a shock pulse to the heart when the device detects fibrillation. Another type of electrical therapy for tachyarrhythmias is anti-tachycardia pacing (ATP). In ATP, the heart is competitively paced with one or more pacing pulses in an effort to interrupt the reentrant circuit causing a tachycardia. ATP can be applied to either the ventricles or the atria. Modern ICD's typically are also pacemakers with ATP capability configured so that ATP therapy is delivered to the heart when a tachycardia is detected, while a shock pulse is delivered when fibrillation occurs.

The delivery of pacing pulses to heart, whether to treat bradycardia or tachycardia, is a transfer of energy that can have deleterious physiological effects if sustained over a long enough period and at a high enough rate. In order to prevent this possibility, it would be desirable for a pacemaker to be configured to monitor the rate at which pacing energy is transferred as well as the cumulative amount of the energy as the pacemaker delivers pacing therapy in different modes.

SUMMARY

A pacing monitoring system is described for incorporation in an implantable pacemaker that monitors the pacing rate and/or cumulative pace count in order to protect a patient from excessive pacing. The system includes monitoring circuitry that is configured to operate in multiple monitoring zones, where each zone is adapted to prevent excessively high-rate pacing during a particular mode of device operation.

DETAILED DESCRIPTION

Figure 1:
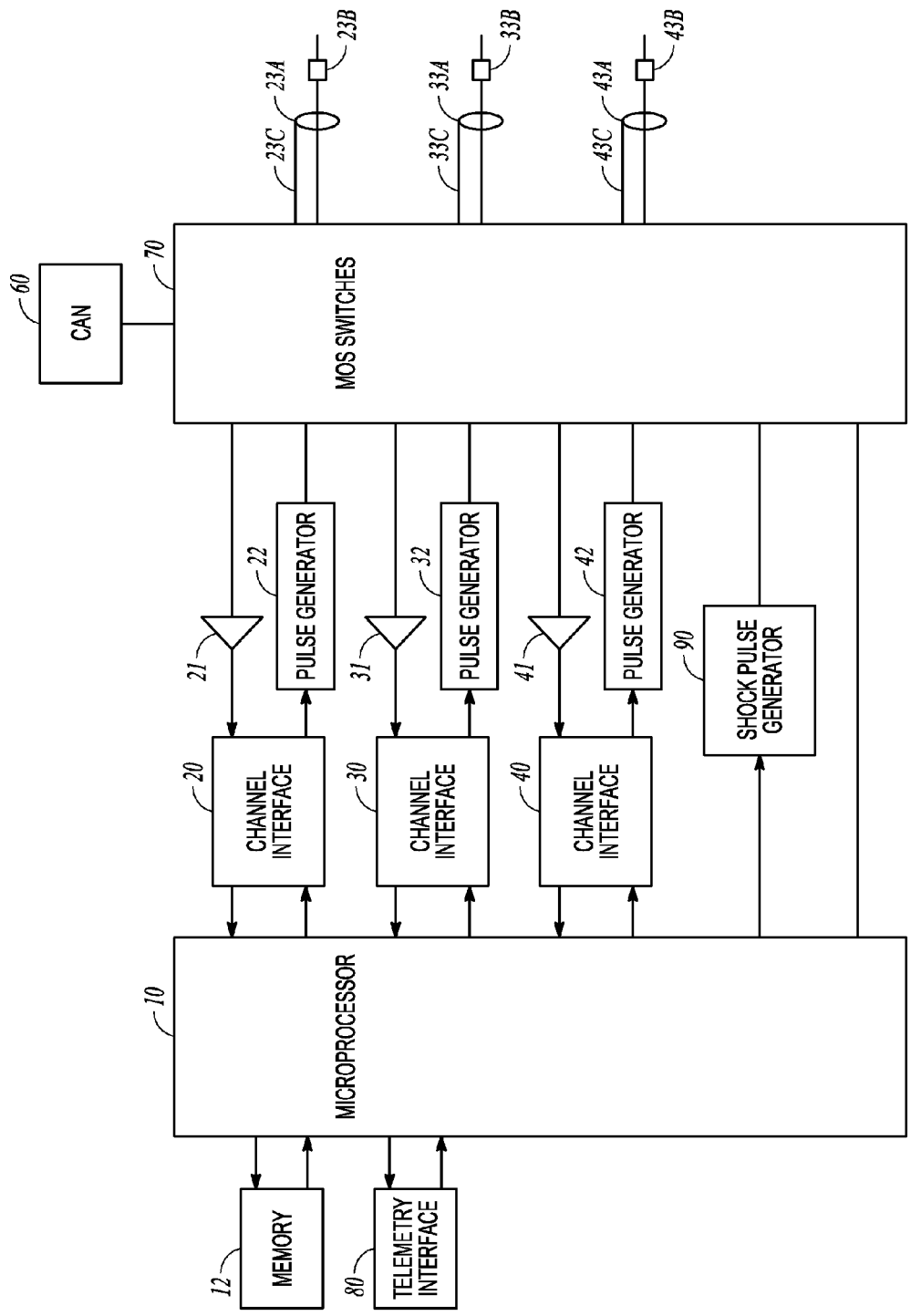
FIG. 1 is a block diagram of a cardiac rhythm management device with ATP and bradycardia pacing capability.

The normal decision on the rate for energy delivery in an implantable pacemaker delivering bradycardia pacing is a complex combination based on the target rate programmed by the patient's physician, detected activity level of the patient, and the current pacing mode of the device. In addition, ATP therapies to treat fast heart rates involve short bursts of rapid pacing into either the atrium or ventricle (depending on where the fast heart rate is detected). Pacemakers may also be configured with other high-rate pacing modes that enable an electro-physiologist to test the patient for certain heart conditions. Although a pacemaker could be configured to simply always limit the pacing rate below a level considered unsafe, any of the types of pacemaker operation just mentioned may require temporary pacing at rates that would be hazardous if sustained for long periods. Simply disabling protection against excessive pacing during such therapy delivery is not a desirable option since that would leave the patient vulnerable to excessively high-rate pacing as a result of erroneous device behavior.

Disclosed herein is a pacemaker that incorporates an adaptable pacing rate monitor to protect the patient from erroneous high-rate pacing. The pacing rate monitor utilizes separate protection zones for different classes of pacing therapy. Such a multiple zone approach adapts the pacing rate protection to the type of therapy being delivered by providing separate protection zones for pacing modes that deliver energy at different rates. The criteria for acceptable pace delivery in each zone are tailored to the therapy requirements for that zone, maximizing the probability of detection of erroneous device behavior. For example, separate zones for high rate pacing into both the atrium and ventricle may be provided, as the hazards associated with each are different. Patient safety is thereby maintained in the presence of device failures while still allowing for delivery of the desired therapy.

In an exemplary embodiment, the pacing rate monitor is capable of operating in four monitoring zones: a normal-rate zone, a high-rate zone, an unlimited-rate zone, and a fail-safe zone. During normal bradycardia pacing, the monitor operates in the normal-rate zone, where a single pacing rate limit is set for both the atrium and ventricles based on a clinically acceptable maximum sustained pacing rate. A pace scheduled to be delivered by the pacing circuitry is blocked if that pace would result in a pacing rate above the pacing rate limit. In addition, a grace interval may be provided to allow a second pace to occur very soon after a first pace, while the heart tissue would be in refractory, even if the pace would occur at an interval after the first pace that would violate the pacing rate limit. No hazard exists if the second pace is delivered into refractory tissue which will not respond to further stimulation. Closely spaced back-up pacing is used in some normal operating modes to ensure capture by a pacing pulse (e.g., auto capture paces and safety paces) and are not blocked in this embodiment. Any additional pace that occurs after the grace interval and exceeds the set high-rate limit, however, will be blocked and an error declared. While the device is delivering ATP therapy in this embodiment, the monitor operates in a high-rate zone that allows a higher pacing rate than the normal-rate zone and also enforces a pace count limit that limits the cumulative number of paces delivered over a specified period time. A high-rate zone may also be useful for performing certain diagnostic testing procedures with pacing stimulation.

Separate atrial and ventricular high-rate zones may be provided for delivering atrial or ventricular ATP therapy so that a higher rate burst of paces is permitted into either the atrium or ventricle while the other chamber is kept in the normal-rate zone. Each high-rate zone may have its own pacing rate limit. For example, the ventricular high-rate zone may allow pacing rates of up to 500 pulses per minute, while the atrial high-rate zone may allow pacing up to 1500 pulses per minute. The grace interval for closely spaced pacing remains operative for the chamber receiving pacing monitored in the normal-rate zone, while no grace interval is used in monitoring the chamber where high-rate delivery is allowed in high-rate zone. The maximum number of paces allowed while in either of these high-rate zones is limited to a specified maximum count limit. Any pace that exceeds the set high-rate limits or exceeds the count limit will be blocked and an error declared. Separate atrial and ventricular high-rate monitoring zones allow a pacemaker to deliver atrial ATP therapy without creating the risk of fast pacing into the ventricle which could trigger ventricular fibrillation. Fast ventricular pacing is required for ventricular ATP and is usually only provided in devices with a high-voltage defibrillator to protect against fatal fast rhythms.

Also in an exemplary embodiment, the pacing monitor may be made to operate in an unlimited-rate zone where no pacing rate limits or pace count limits are enforced. The unlimited-rate zone is useful for certain tests performed under the supervision of an electro-physiologist. In this zone, pacing is limited to a time period (e.g., 2 seconds) after which an error is declared. The time-limit of the unlimited-rate zone may be configured to be restarted a specified maximum number of times by a manually input (i.e., via a telemetry) signal. A fail-safe zone is activated in response to a system-reset or an error in any of the other monitor zones. The fail-safe zone has the same characteristics as the normal-rate zone, but has a lower pacing rate limit (e.g., 100 paces per minute). Transitions between monitoring zones are under program control in response to certain events or to telemetry commands. Digital keys may be used to protect against unintended transitions between zones.

1. Exemplary Pacemaker

FIG. 1 is a system diagram of a microprocessor-based cardiac rhythm management device with the capability of delivering bradycardia or anti-tachycardia pacing therapy to either the ventricles or the atria and in which may be incorporated a pacing monitor as described above. Pacemakers are usually implanted subcutaneously on the patient's chest and connected to electrodes by leads threaded through the vessels of the upper venous system into the heart. An electrode can be incorporated into a sensing channel that generates an electrogram signal representing cardiac electrical activity at the electrode site and/or incorporated into a pacing or shocking channel for delivering pacing or shock pulses to the site.

The controller of the device is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the term circuitry should be taken to mean either the programming of a controller in the form of executable code stored in memory or other storage medium or to discrete logic circuitry configured to perform particular functions. The controller is capable of operating the device so as to deliver a number of different therapies in response to detected cardiac activity. A telemetry interface 80 is also provided for enabling the controller to communicate with an external programmer or other device via a wireless telemetry link.

The device shown in FIG. 1 has three sensing/pacing channels, where a pacing channel is made up of a pulse generator connected to an electrode while a sensing channel is made up of the sense amplifier connected to an electrode. A MOS switch matrix 70 controlled by the microprocessor is used to switch the electrodes from the input of a sense amplifier to the output of a pulse generator. The switch matrix 70 also allows the sensing and pacing channels to be configured by the controller with different combinations of the available electrodes. A shock pulse generator 90 is also interfaced to the controller for delivering defibrillation shocks between an electrode and the housing or can 60 as selected by the switch matrix. In an example configuration, a sensing/pacing channel may include ring electrode 43*a* (33*a* or 23*a*) and tip electrode 43*b* (33*b* or 23*b*) of bipolar lead 43*c* (33*c* or 23*c*), sense amplifier 41 (31 or 21), pulse generator 42 (32 or 22), and a channel interface 40 (30 or 20). The channel interfaces communicate bi-directionally with a port of microprocessor 10 and may include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. In the illustrated embodiment, the device is equipped with bipolar leads that include two electrodes which are used for outputting a pacing pulse and/or sensing intrinsic activity. Other embodiments may employ unipolar leads with single electrodes for sensing and pacing which are referenced to the device housing or can 60 (or another electrode) by the switch matrix 70. The channels may be configured as either atrial or ventricular channels so as to enable either biatrial or biventricular pacing. For example, a configuration for biventricular sensing/pacing could have one lead of a channel disposed in the right ventricle for right ventricular sensing/pacing and another lead of a channel disposed in the coronary sinus for left ventricular sensing/pacing.

The controller controls the overall operation of the device in accordance with programmed instructions stored in memory, including scheduling the delivery of paces via the pacing channels, interpreting sense signals received from the sensing channels, and implementing timers for defining escape intervals. The sensing circuitry of the pacemaker detects a chamber sense when an electrogram signal (i.e., a voltage sensed by an electrode representing cardiac electrical activity) generated by a particular channel exceeds a specified intrinsic detection threshold. Pacing algorithms used in particular pacing modes employ such senses to trigger or inhibit pacing. Both bradycardia and anti-tachycardia pacing modes may be implemented in code executed by the controller.

Bradycardia pacing modes refer to pacing algorithms which are used to pace the atria and/or ventricles in a manner that enforces a certain minimum heart rate or restores AV conduction. Bradycardia pacing modes are also used to deliver cardiac resynchronization pacing. Because of the risk of inducing an arrhythmia with asynchronous pacing, most pacemakers when delivering bradycardia pacing are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. In a triggered mode, a sense occurring in one heart chamber triggers a pace to either the same or a different heart chamber. For example, in an atrial tracking mode, an atrial sense triggers an escape interval that results in a ventricular pace upon expiration.

The device of FIG. 1 may also deliver ATP therapy and be programmed with a plurality of selectable ATP pacing protocols that define the manner in which anti-tachycardia pacing is delivered. In a microprocessor-based device, the output of pacing pulses is controlled by a pacing routine that implements the selected pacing protocol as defined by various parameters. A data structure stored in memory contains the parameter sets that define each of the available pacing protocols. Pacing protocols for ATP therapy attempt to block the reentrant depolarization wave front causing the tachycardia with depolarizing wave fronts produced by a burst of pacing pulses. Protocols may vary according to parameters that define the number of pulses delivered and the particular timing employed. For example, the protocol may define a burst of pulses delivered at a specified pacing interval (or with varying pacing intervals) and for a specified time. The protocol may further define the duration and amplitude of the pacing pulses. Different protocols are apt to be more successful than others in terminating particular tachyarrhythmias that may differ as to rate and/or depolarization pattern. For this reason, modern cardiac rhythm management devices are capable of employing a number of different ATP protocols to deliver therapy, all of which involve the delivery of pacing pulses at a rapid rate for a short period of time.

2. Pacing Rate Monitoring System and Operation

Figure 2:
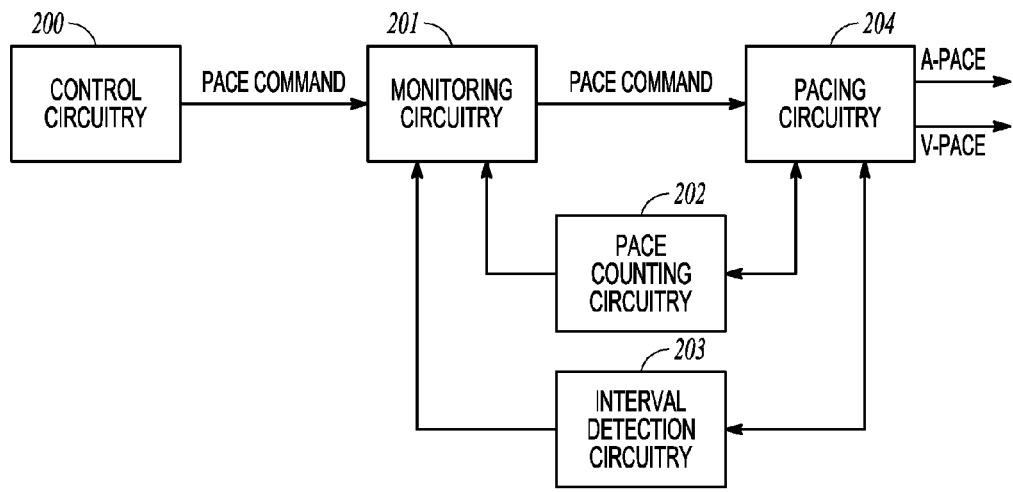
FIG. 2 illustrates the components of an exemplary pacing monitoring system.

FIG. 2 shows the components of an exemplary pacing monitoring system that may be incorporated into an implantable pacemaker such as shown in FIG. 1. The circuitry to be described may be implemented as code executed by microprocessor-based controller, as discrete circuit components, or as some combination thereof. For example, in one embodiment, the monitoring circuitry 201 is a separate circuit component in communication with and under the control of the microprocessor-based controller. The pacing control circuitry 200 schedules atrial and ventricular paces (A-paces and V-paces, respectively) in accordance with a bradycardia pacing algorithm, an ATP protocol, or in response to commands received via telemetry. When a pace is scheduled by the pacing control circuitry, an A-pace or V-pace command is issued to the monitoring circuitry 201 which, if the scheduled pace is not to be blocked, then passes the command to pacing circuitry 204. Pacing circuitry 204 represents those components of the device that actually generate and deliver a pacing pulse to heart, either as an A-pace or V-pace. Monitoring circuitry 201 also receives inputs from pace counting circuitry 202 and interval detection circuitry 203. Pace counting circuitry 202 maintains a count of the total number of atrial and ventricular paces delivered by the pacing circuitry 204 over a specified period of time or since a specified event such as a change in pacing mode. Other embodiments may maintain separate pace counts for different heart chambers. Interval detection circuitry measures the time interval from the last pace delivered by the pacing circuitry 204 for atrial and/or ventricular paces. The reciprocal of the intervals from the last atrial or ventricular paces to next scheduled atrial or ventricular pace represents the instantaneous atrial or ventricular pacing rate, respectively, were the scheduled pace to be delivered. Other embodiments may measure intervals since the last pace for other heart chambers (e.g., right and left ventricles) to derive separate pacing rates for those chambers. Based upon the pace count and pacing intervals received from the counting and interval detection circuitry, the monitoring circuitry makes a pacing decision whether to block the scheduled pace or pass the pace command to the pacing circuitry 204. As described below, the pacing decision is made in a manner that depends upon the monitoring zone that the monitoring circuitry is operating in.

In order to provide the pacemaker with protection against erroneous high-rate pacing and/or excessive delivery of pacing energy to the heart, the monitoring circuitry is designed to operate in two or more monitoring zones. One of the zones is the normal-rate zone for use during normal bradycardia pacing. When operating in the normal-rate zone, the monitoring circuitry is configured to set an error flag if the pacing rate exceeds a specified normal-rate limit value. As used herein, an error flag is any signal or indication to signify that the monitoring circuitry has detected an error condition. Another monitoring zone is the high-rate zone for use during ATP pacing, as well as certain test modes where bursts of high-rate pacing are employed. When operating in the high-rate zone, the monitoring circuitry is configured to set an error flag if either the pacing rate exceeds a specified high-rate limit value or if the pace count exceeds a specified count limit value. In the normal-rate zone, the monitoring circuitry may be configured to block the delivery of a scheduled pace that would exceed the normal-rate limit value and thereby causes the setting of an error flag. Similarly, in the high-rate zone, the monitoring circuitry may be configured to block delivery of a scheduled pace that would exceed the high-rate limit value or the count limit value and thereby causes the setting of an error flag. The monitoring circuitry in the normal-rate zone may be configured to permit, without setting an error flag, delivery of a pace during a specified grace interval after the preceding pace without regard to the specified rate limit value. The device may also incorporate circuitry to cause the monitoring circuitry to automatically operate in the normal-rate zone if pacing is being delivered in a bradycardia pacing mode and to operate in the high-rate zone if the pacing is being delivered in an anti-tachycardia pacing mode.

In one particular embodiment, where the device is configured to deliver ATP or other high-rate pacing to either the atria or ventricles, the monitoring circuitry is capable of simultaneously operating in either an atrial high-rate zone and a ventricular normal-rate zone or a ventricular high-rate zone and an atrial normal-rate zone. When operating in the atrial high-rate zone and ventricular normal-rate zone, the monitoring circuitry sets an error flag if either 1) the atrial pacing rate exceeds a specified atrial high-rate limit value or if the pace count exceeds the specified count limit value or 2) if the ventricular pacing rate exceeds the normal-rate limit value. Similarly, when operating in the ventricular high-rate zone and atrial normal-rate zone, the monitoring circuitry sets an error flag if either 1) the ventricular pacing rate exceeds a specified ventricular high-rate limit value or if the total pace count exceeds the specified count limit value or 2) the atrial pacing rate exceeds the normal-rate limit value. The device may also include circuitry to cause the monitoring circuitry to operate in the normal-rate zone if pacing is being delivered in a bradycardia pacing mode and to cause the monitoring circuitry to operate in the atrial high-rate zone and the ventricular normal-rate zone if the pacing is being delivered in an atrial anti-tachycardia pacing mode and in the ventricular high-rate zone and atrial normal-rate zone if the pacing is being delivered in a ventricular anti-tachycardia pacing mode. The monitoring circuitry may also be configured to block delivery of a scheduled pace that would exceed the normal-rate limit value, the atrial high-rate limit value, the ventricular high-rate limit value, or the specified count limit value and that results in the setting of an error flag.

In another particular embodiment, the pacing circuitry of the device is capable of delivering pacing pulses to first and second heart chambers in accordance with a programmed pacing mode, where the first and second heart chambers could be the right and left ventricles (or atria). The interval detection circuitry is configured to measure the interval between the times of a scheduled pace and a preceding delivered pace for both first chamber and second chamber paces and derive a first chamber pacing rate and a second chamber pacing rate therefrom. The counting circuitry is configured to count the number of first chamber and second chamber pacing pulses delivered over a specified time period and derive a total pace count therefrom (which may also include atrial paces). The monitoring circuitry is then configured to operate in either a normal-rate zone or a high-rate zone for both chambers.

In another embodiment, a fail-safe monitoring zone is provided in addition to normal-rate and high-rate zones, where the monitoring circuitry transitions to the fail-safe zone whenever an error flag is set is one of the other zones. The fail-safe zone has a specified fail-safe rate limit value, and the monitoring circuitry prevents scheduled paces from being delivered above the specified fail-safe rate limit value when operating in the fail-safe rate zone. The monitoring circuitry may be made further capable of operating in an unlimited-rate zone in which no rate limit values or count limit values are imposed that may be used for electrophysiological testing. The monitoring circuitry is caused to transition to the unlimited-rate zone upon receipt of an unlimited-rate zone command by the telemetry circuitry of the device and remains in the unlimited-rate zone for a specified test duration (e.g. 2 seconds). An error flag is set after the specified test duration expires at which point the monitoring circuitry reverts to the fail-safe zone. In a particular embodiment, the monitoring circuitry remains in the unlimited-rate zone for as long as an unlimited-rate zone command is continually received up to a specified clinical duration that is greater than the specified test duration (e.g., 30 seconds). For example, the unlimited-rate command may be issued from an external programmer when a clinician presses a particular key or button. As long as the key is depressed, an unlimited-rate zone command is continually transmitted so that the monitoring circuitry remains in the unlimited-rate zone until the either the key is released or the specified clinical duration expires.

Figure 3:
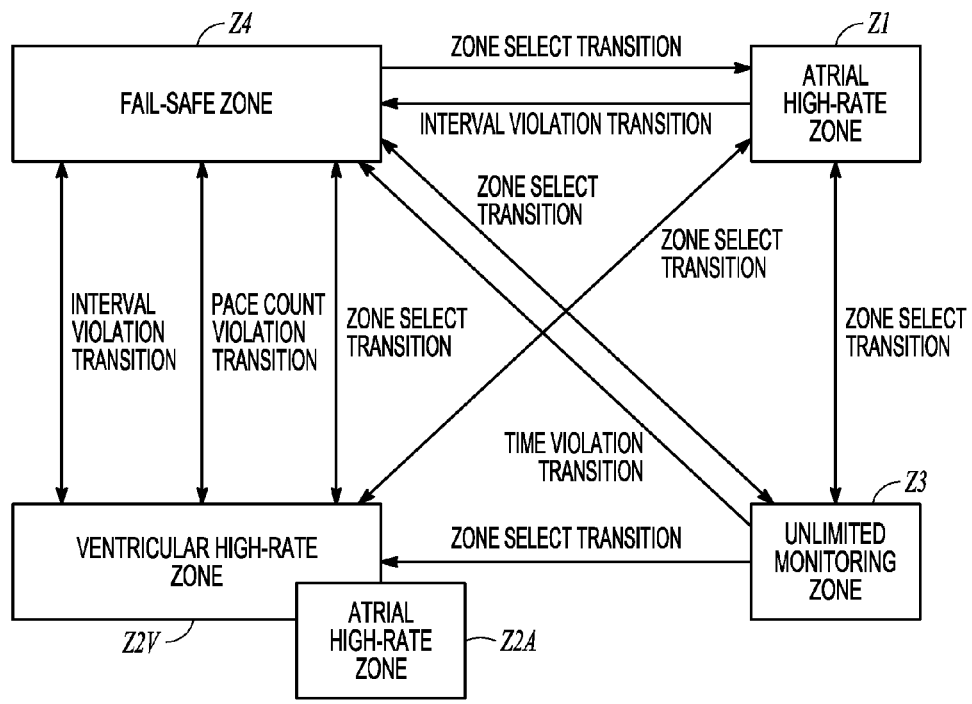
FIG. 3 illustrates different monitoring zones according to an exemplary embodiment.

FIG. 3 illustrates the monitoring zones just described that the monitoring circuitry is configured to operate in according to one embodiment: a normal-rate zone Z1, a ventricular high-rate zone Z2v, an atrial high-rate zone Z2a, an unlimited-rate zone Z3, and a fail-safe zone Z4. As shown in the figure, the circuitry transitions from the normal-rate zone to the fail-safe zone upon occurrence of an interval violation, and transitions from the atrial or ventricular high-rate zone to the fail-safe zone upon occurrence of either an interval violation or a pace count violation. A time violation causes the monitoring circuitry to transition from the unlimited-rate zone to the fail-safe zone. The device may be configured so that the monitoring circuitry is caused to transition to any selected zone upon receipt of a zone select transition command via telemetry and/or is automatically caused to transition to appropriate zone or zones depending upon the type of pacing being delivered.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A method for operating a cardiac rhythm management device, comprising:
    scheduling paces to be delivered by pacing circuitry in accordance with a programmed pacing mode;
    measuring the interval between the times of a scheduled pace and a preceding delivered pace, the reciprocal of the interval being the pacing rate;
    counting the number of pacing pulses delivered over a specified time period and deriving a pace count therefrom;
    monitoring the pacing rate and the pace count in either a normal-rate zone or a high-rate zone;
    when operating in the normal-rate zone, setting an error flag if the pacing rate exceeds a specified normal-rate limit value; and,
    when operating in the high-rate zone, setting an error flag if either the pacing rate exceeds a specified high-rate limit value or if the pace count over the specified period of time exceeds a specified count limit value.

2. The method of claim 1 further comprising blocking delivery of a scheduled pace that would exceed the normal-rate limit value.

3. The method of claim 1 further comprising blocking delivery of a scheduled pace that would exceed the high-rate limit value.

4. The method of claim 1 further comprising blocking delivery of a scheduled pace that would exceed the count limit value.

5. The method of claim 1 further comprising blocking delivery of a scheduled pace that results in the setting of an error flag.

6. The method of claim 1 further comprising operating in the normal-rate zone if pacing is being delivered in a bradycardia pacing mode.

7. The method of claim 1 further comprising operating in the high-rate zone if the pacing is being delivered in an anti-tachycardia pacing mode 8. The method of claim 1 further comprising:
    delivering atrial and ventricular pacing pulses in accordance with a programmed pacing mode;
    measuring the interval between the times of a scheduled pace and a preceding delivered pace for both atrial and ventricular paces, the reciprocal of the intervals being the atrial pacing rate and the ventricular pacing rate;
    counting the number of atrial and ventricular pacing pulses delivered over a specified time period and derive a total pace count therefrom;
    operating in either an atrial high-rate zone and a ventricular normal-rate zone or a ventricular high-rate zone and an atrial normal-rate zone;
    when operating in the atrial high-rate zone, setting an error flag if the atrial pacing rate exceeds a specified atrial high-rate limit value; and,
    when operating in the ventricular high-rate zone, setting an error flag if the ventricular pacing rate exceeds a specified ventricular high-rate limit value.

9. The method of claim 8 further comprising, when operating in the atrial high-rate zone, setting an error flag if the pace count over the specified period of time exceeds the specified count limit value.

10. The method of claim 8 further comprising, when operating in the ventricular high-rate zone, setting an error flag if the total pace count over the specified period of time exceeds the specified count limit value.

11. The method of claim 8 further comprising blocking delivery of a scheduled pace that would exceed the normal-rate limit value, the atrial high-rate limit value, the ventricular high-rate limit value, or the specified count limit value and that results in the setting of an error flag.

12. The method of claim 8 further comprising operating in the normal-rate zone if pacing is being delivered in a bradycardia pacing mode and operating in the atrial high-rate zone if the pacing is being delivered in an atrial anti-tachycardia pacing mode and in the ventricular high-rate zone if the pacing is being delivered in a ventricular anti-tachycardia pacing mode.

13. The method of claim 1 further comprising operating in a fail-safe zone having a specified fail-safe rate limit value, wherein the fail-safe zone is transitioned to when an error flag is set, and preventing scheduled paces from being delivered above the specified fail-safe rate limit value if the fail-safe rate zone is in operation.

14. The method of claim 13 further comprising operating in an unlimited-rate zone in which no rate limit values or count limit values are imposed.

15. The method of claim 14 further comprising:
entering the unlimited-rate zone upon receiving an unlimited-rate zone command via telemetry and remaining in the unlimited-rate zone for a specified test duration; and, setting an error flag after the specified test duration expires and then reverting to the fail-safe zone.

16. The method of claim 14 further comprising remaining in the unlimited-rate zone for as long as an unlimited-rate command is continually received up to a specified clinical duration that is greater than the specified test duration.

17. The method of claim 14 further comprising transitioning to any of the normal-rate, high-rate, unlimited-rate, or fail-safe zones upon receipt of a zone select transition command via telemetry.

18. The method of claim 1 further comprising permitting, without setting an error flag, delivery of a single pace during a specified grace interval after the preceding pace without regard to the specified rate limit value when in the normal-rate zone.

19. The method of claim 1 further comprising entering the high-rate zone upon receiving a high-rate zone command via telemetry.

20. The method of claim 1 further comprising:
delivering pacing pulses to first and second heart chambers in accordance with a programmed pacing mode;
measuring the interval between the times of a scheduled pace and a preceding delivered pace for both first chamber and second chamber paces, the reciprocal of the intervals being the first chamber pacing rate and the second chamber pacing rate;
counting the number of first chamber and second chamber pacing pulses delivered over a specified time period and derive a total pace count therefrom; and,
operating in either a normal-rate zone or a high-rate zone for both of the first and second chambers.

* * * * *